(12) United States Patent
Utagawa (10) Patent No.: US 8,678,590 B2
(45) Date of Patent: Mar. 25, 2014

(54) APPARATUS AND METHOD FOR IMAGING OPTICAL COHERENCE TOMOGRAPHIC IMAGE

(75) Inventor: Tsutomu Utagawa, Yokohama (JP)

(73) Assignee: Canon Kabushiki Kaisha, Tokyo (JP)

( * ) Notice: Subject to any disclaimer, the term of this patent is extended or adjusted under 35 U.S.C. 154(b) by 259 days.

(21) Appl. No.: 12/944,621

(22) Filed: Nov. 11, 2010

(65) Prior Publication Data

US 2011/0116045 A1    May 19, 2011

(30) Foreign Application Priority Data

Nov. 17, 2009   (JP) ................................. 2009-262394

(51) Int. Cl.
*A61B 3/14* (2006.01)
*A61B 3/10* (2006.01)

(52) U.S. Cl.
USPC ............................ 351/210; 351/205; 351/212

(58) Field of Classification Search
USPC ................ 351/210, 246, 205, 208, 209, 212; 385/1–3, 40, 129–132, 5, 8–9
See application file for complete search history.

(56) References Cited

U.S. PATENT DOCUMENTS

| 2005/0270486 | A1 | 12/2005 | Teiwes | |
|---|---|---|---|---|
| 2010/0118132 | A1* | 5/2010 | Yumikake et al. | 348/78 |
| 2010/0195050 | A1 | 8/2010 | Sakagawa | |

FOREIGN PATENT DOCUMENTS

| EP | 1808119 A1 | 7/2007 |
|---|---|---|
| EP | 1882445 A2 | 1/2008 |
| JP | 2008-104628 A | 5/2008 |
| WO | WO2006/052479 A2 | 5/2006 |

* cited by examiner

*Primary Examiner* — Dawayne A Pinkney
(74) *Attorney, Agent, or Firm* — Canon U.S.A., Inc., IP Division (57) ABSTRACT

An ophthalmic imaging apparatus for imaging a subject's eye includes a detection unit configured to detect facts that the subject's eye moves by an amount of movement thereof, which is equal to or more than a predetermined value, and that the movement thereof is finished, and an imaging start unit configured to start imaging of the subject's eye according to a result of detection by the detection unit.

26 Claims, 5 Drawing Sheets

|         | TIME-PERIOD | CYCLE     | DISPLACEMENT |
|---------|-------------|-----------|--------------|
| DRIFT   | 0.2~1s      |           | 7~17Hz       |
| TREMOR  |             | 30~100Hz  | 0.3~3.5Hz    |
| FLICK   | 10~30ms     | 0.2~2Hz   | 7~52Hz       |

APPARATUS AND METHOD FOR IMAGING OPTICAL COHERENCE TOMOGRAPHIC IMAGE

BACKGROUND OF THE INVENTION

1. Field of the Invention

The present invention relates to an apparatus and method for imaging an optical coherence tomographic image and, more particularly, to an imaging apparatus and method for use in an ophthalmic field.

2. Description of the Related Art

Currently, various ophthalmic apparatuses using optical devices are used. Such apparatuses are, e.g., an anterior eye camera, a fundus camera, and a confocal scanning laser ophthalmoscope (scanning laser ophthalmoscope (SLO)). Particularly, an optical coherence tomographic imaging apparatus (hereinafter referred to as an OCT apparatus) is configured to obtain a tomographic image of an inspection target at high resolution, and is becoming an indispensable apparatus in clinics dedicated to retinal outpatients. The above OCT apparatus uses a low-coherence light-source as a source of light. Light from the light-source is split into measurement light and reference light through a split optical path such as a beam splitter. With one of such split-light components, i.e., the measurement light, an inspection target such as an eye via a measurement optical path is irradiated. Return light thereof is guided to a detection position via a detection optical path. The return light is reflected light or scattered light, which contains information concerning an interface in a direction of light-irradiating of the inspection target. The other light component, i.e., the reference light is reflected by a reference mirror or the like via a reference optical path, and guided to the detection position. The return light and the reference light are caused to interfere with each other. Interference light generated therebetween is guided to a photoelectric conversion element such as a charge-coupled device (CCD) line sensor or a complementary metal-oxide semiconductor (CMOS) line sensor via an optical element such as a spectroscope. Then, wavelength spectra are collectively output therefrom as electric signals. The electric signals output in the above manner are converted by an analog-to-digital (A/D) converter into digital signals. In addition, the digital signals obtained by A/D conversion are subjected to a Fourier transform. Consequently, a tomographic image of the inspection target can be obtained. This method is referred to as a spectrum domain (hereinafter referred to as SD) method.

If a retina is employed as the inspection target in the OCT apparatus, a three-dimensional (3D) image of the retina can be acquired by scanning measurement light on the retina using a Galvano mirror or the like. However, if image information is acquired by setting, as the inspection target, a part of an eyeball such as a retina, it is difficult to accurately acquire image information concerning the eyeball, because of a subject's involuntary eye movement during visual-fixation. Thus, Japanese Patent Application Laid-Open No. 2008-104628 proposes an apparatus for imaging a conjunctiva and a sclera of a subject's eye by excluding effects of the subject's involuntary eye movement during visual-fixation.

The apparatus proposed in Japanese Patent Application Laid-Open No. 2008-104628 employs a system configured to exclude effects of the subject's involuntary eye movement during visual-fixation according to a method of adjusting a position of an imaging area corresponding to each taken image by following the subject's involuntary eye movement during visual-fixation, using a camera capable of imaging a target at a rate of 200 frames per second (fps). However, in order to acquire a 3D-image of an ocular-fundus, according to the system discussed in Japanese Patent Application Laid-Open No. 2008-104628, hundreds milliseconds (ms) are taken to acquire a single 3D-image. That is, about only two 3D-images can be acquired per second, as will be described below. Thus, according to the system discussed in Japanese Patent Application Laid-Open No. 2008-104628, it is difficult to eliminate effects of the subject's involuntary eye movement upon an image during visual-fixation, particularly, effects of a flick thereupon causing a largest displacement of a retina among the motions of the subject's involuntary eye movement during visual-fixation.

Figure 2A:
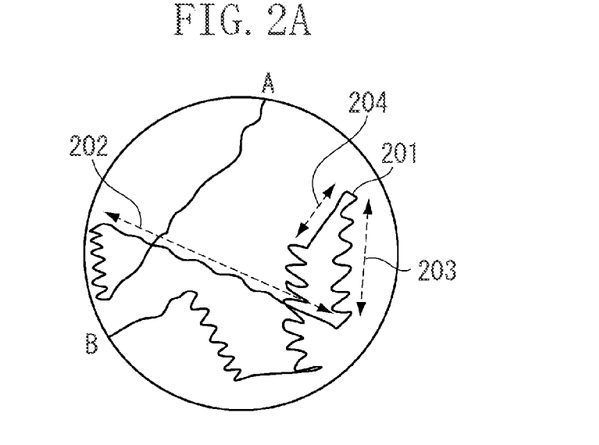
FIGS. 2A, 2B, and 2C illustrate a subject's involuntary eye movement during visual-fixation.
Figure 2B:
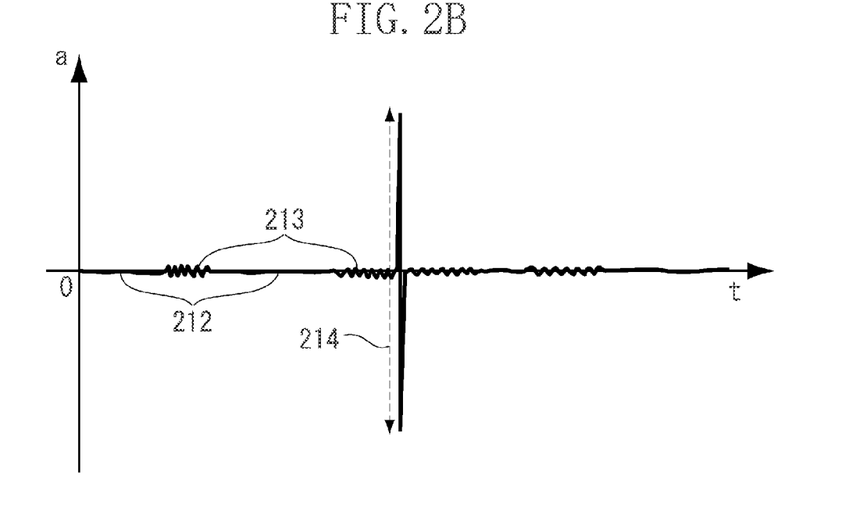
Figure 2C:
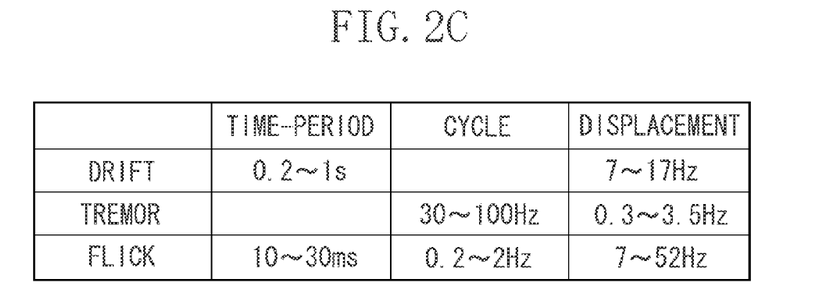

Hereinafter, these problems are described in detail. FIGS. 2A through 2C illustrate aspects of a subject's involuntary eye movement during visual-fixation. In FIG. 2A, a solid curve 201 represents a trajectory of the center of the retina of the subject's eye. As illustrated in FIG. 2A, the retinal center initially positioned at point A moves to point B through paths that are represented by two-headed dashed arrows 202, 203, and 204 and generated by the subject's involuntary eye movement during visual-fixation. Usually, the involuntary eye movement includes a combination of the following three motions, i.e., a drift 202 in which the retinal center moves at low speed, a tremor 203 in which the retinal center repeats fine zigzag movements, and a flick 204 in which the retinal center instantaneously moves. In order to describe features of the subject's involuntary eye movement during visual-fixation, FIG. 2B illustrates the movement of the retinal center, which has been illustrated in FIG. 2A, by setting an abscissa axis and an ordinate axis to represent time, and acceleration in a direction of a y-axis (vertical direction) of a position of the retinal center, respectively. The retina operates in two-dimensional directions, i.e., a horizontal direction and a vertical direction, respectively, due to the involuntary eye movement during visual-fixation. For brevity of description, only an operation in the vertical direction is described. As illustrated in FIG. 2B, accelerations 212 are obtained where a drift is performed. Accelerations 213 are obtained where a tremor is performed. Accelerations 214 are obtained where a flick is performed. FIG. 2C illustrates the features of the three motions included in the involuntary eye movement during visual-fixation.

The drift is a small motion that substantially always occurs and that causes a retinal displacement of 7 µm through 17 µm in a time-period of 0.2 seconds (s) through 1 s. The tremor is a slight quiver that occurs periodically every period corresponding to a frequency of 30 Hertzes (Hz) through 100 Hz, i.e., every period of 10 ms through 33 ms and that causes a retinal displacement of 0.3 µm through 3.5 µm. The flick is an abrupt motion that occurs periodically every period corresponding to a frequency of 0.2 Hz through 2 Hz, i.e., every period of 500 ms through 5 s and that causes a retinal displacement of 7 µm through 52 µm in a time-period of 10 ms through 30 ms.

Hereinafter, it is described a case of acquiring a 3D-image of an ocular-fundus by setting a scanning area of 6 millimeters (mm)×6 mm and a resolution corresponding to a size of 20 µm×20 µm, using the apparatus discussed in Japanese Patent Application Laid-Open No. 2008-104628. It is assumed that interference light dispersed by a spectroscope is subjected to photoelectric conversion using a high-speed line camera at a line rate of 250 kilo-Hz (kHz), and that 20% of a time-period in which the ocular-fundus is two-dimensionally scanned using a Galvano mirror, is unavailable for reading a 3D-image of the ocular-fundus. In this case, time T required to read the 3D-image is given by:

$$T=(6/(20*10^{-3}))^2/(250*10^3)/0.8=450 \text{ ms}.$$

When a 3D-image of the ocular-fundus is acquired on the above conditions, among the motions of the involuntary eye movement during visual-fixation, the drift and the tremor are not so problematic in acquiring a 3D-image, in view of the resolution and the displacement per unit time. However, if a flick occurs in a time-period of 450 ms, which is required to acquire a 3D-image, a position of an eye is extremely displaced in a short time. Accordingly, continuity of a read image cannot be assured. Consequently, an accurate 3D-image thereof cannot be acquired. According to the method using a camera capable of imaging at a rate of 200 fps, it is difficult to eliminate effects of the involuntary eye movement upon an image during visual-fixation, particularly, effects of a flick thereupon causing a largest displacement of a retina among the motions of the subject's involuntary eye movement during visual-fixation.

SUMMARY OF THE INVENTION

The present invention is directed to an imaging apparatus and method capable of acquiring a 3D-image of an ocular-fundus by suppressing effects upon an image, of a flick causing a largest displacement of a retina among the motions of an inspection-target's involuntary eye movement during visual-fixation. According to the present invention, a 3D-image of an ocular-fundus can be acquired by suppressing effects upon an image, of a flick causing a largest displacement of a retina among the motions of an inspection-target's involuntary eye movement during visual-fixation.

Further features and aspects of the present invention will become apparent from the following detailed description of exemplary embodiments with reference to the attached drawings.

BRIEF DESCRIPTION OF THE DRAWINGS

The accompanying drawings, which are incorporated in and constitute a part of the specification, illustrate exemplary embodiments, features, and aspects of the invention and, together with the description, serve to explain the principles of the invention.

DESCRIPTION OF THE EMBODIMENTS

Various exemplary embodiments, features, and aspects of the invention will be described in detail below with reference to the drawings.

Modes for carrying out the present invention are described with reference to the following exemplary embodiments. However, the present invention is not limited to configurations of the following exemplary embodiments.

Figure 1:
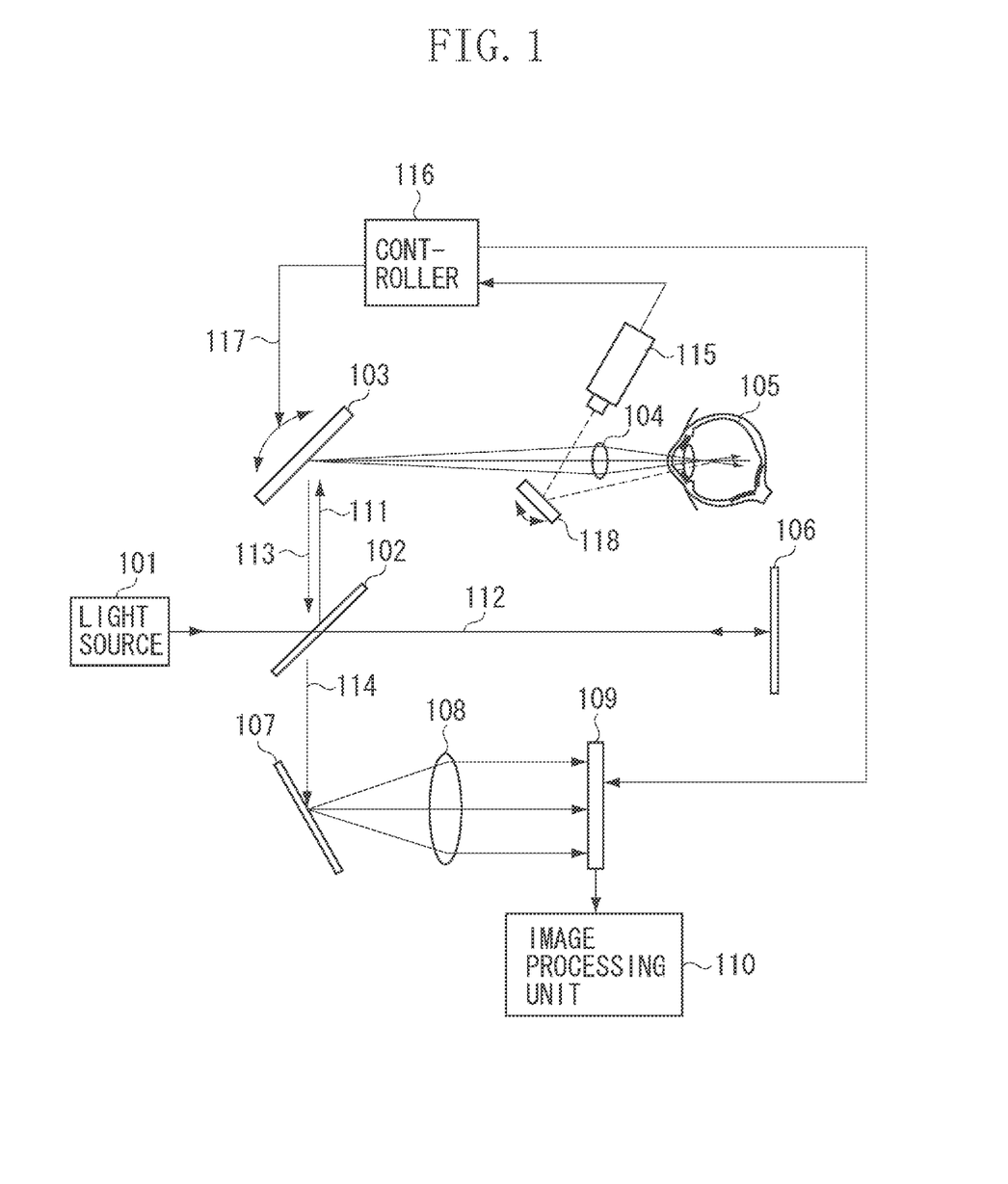
FIG. 1 is a block diagram illustrating a configuration of an SD-OCT apparatus, which is an example of a configuration of an imaging apparatus for imaging an optical coherence tomographic image according to a first exemplary embodiment of the present invention.

Hereinafter, an SD-OCT apparatus serving as an example of an ophthalmic OCT apparatus, to which an imaging apparatus for imaging an optical coherence tomographic image according to the present invention is applied, is described with reference to FIG. 1 as a first exemplary embodiment according to the present invention. FIG. 1 is a block diagram illustrating a configuration of an SD-OCT apparatus according to the present exemplary embodiment. As illustrated in FIG. 1, light output from a light source 101 is split by a beam splitter 102 into reference light 112 and measurement light 111.

The measurement light 111 is guided via a measurement optical-path to an eye 105 serving as an inspection target. Then, the measurement light 111 is reflected or scattered to be returned to the beam splitter 102 as return light 113. After that, the returned light 113 is combined with the reference light 112 via a reference optical-path by the beam splitter 102 into interference light 114.

The interference light 114 is dispersed by a diffraction grating 107. Then, an image is formed on a line sensor 109 by a lens 108.

In this apparatus, a CCD line sensor is used as the line sensor 109. However, a CMOS line sensor can be used as the line sensor 109 without problems. Image information (optical coherence tomographic information) photoelectrically converted at the line sensor 109 is subjected to A/D conversion at an image information processing unit 110. A tomographic image of the eye 105 can be obtained by a Fourier transform of digitalized image information.

Next, the light source 101 and related matters are described.

The light source 101 is a super luminescent diode (SLD) which is a typical low-coherence light source. The light source 101 outputs light which is 840 nanometers (nm) in wavelength and 50 nm in bandwidth. The bandwidth affects a resolution in a direction of an optical axis of an obtained tomographic image and is, therefore, an important parameter. In the present exemplary embodiment, the SLD is selected as the type of the light source. As long as the light source can output low coherence light, any other type of a light source, such as an amplified spontaneous emission (ASE) type light source can be used as the light source 101. In view of a fact that output light of the light source 101 is used for ocular measurement, near-infrared wavelengths are suitable for the wavelength of the light to be output from the light source 101. In addition, the wavelength of the output light affects a resolution in a lateral direction of the obtained tomographic image. Accordingly, it is preferable that the wavelength of the output light is as short as possible. In the present exemplary embodiment, the wavelength of the output light is set at 840 nm. Apparently, depending on a measurement region of an inspection target, other wavelengths can be selected as the wavelength of the output light of the light source 101.

Next, an optical path of the reference light 112 is described hereinafter.

The reference light obtained by splitting the output light of the light source 101 at the beam splitter 102 is reflected by a mirror 106 and returned to the beam splitter 102.

A length of this optical path is set to be the same as that of an optical path of the measurement light 111. Accordingly, the reference light 112 and the measurement light 111 can be caused to interfere with each other.

Next, the optical path of the measurement light 111 is described.

The measurement light 111 obtained by splitting the output light of the light source 101 at the beam splitter 102 is incident upon a mirror of an XY-scanner 103.

In FIG. 1, for simplicity of drawing, the XV-scanner 103 is illustrated as a single mirror.

However, actually, two mirrors, i.e., an X-scanning mirror and a Y-scanning mirror are arranged close to each other. The XY-scanner 103 performs raster scan on the retina of the eye 105 via a lens 104 in two-dimensional directions perpendicular to an optical axis thereof.

The XY-scanner 103 starts a scanning operation according to a start-up signal 117 output from a controller 116 which will be described below. The lens 104 focuses the measurement light 111 onto the retina.

Figure 3:
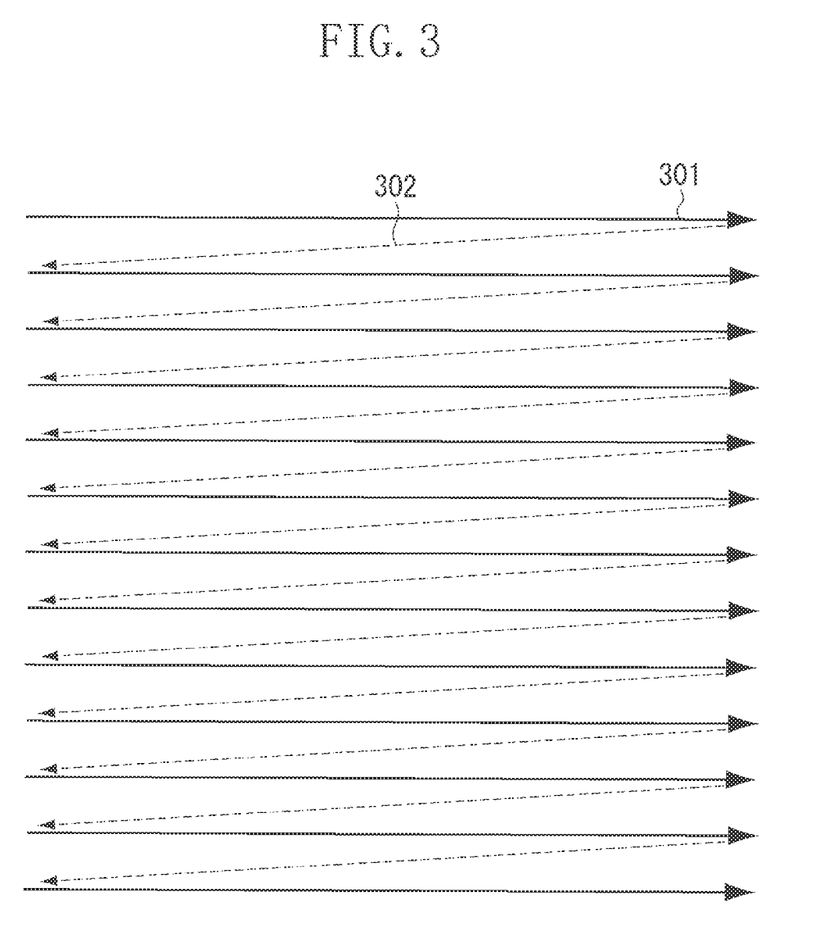
FIG. 3 illustrates a manner in which the SD-OCT apparatus according to the first exemplary embodiment of the present invention performs raster scan on a retina with measurement light.

FIG. 3 illustrates a manner in which the SD-OCT apparatus according to the present exemplary embodiment performs raster scan on the retina.

As indicated by each solid arrow 301 in FIG. 3, in order to read an image of a retina, the retina is scanned with a beam of the measurement light 111 while shifting in parallel at a predetermined speed.

Generally, a planar image acquired by performing such scanning on a retina so as to cut the retina by a plane is referred to as a B-scan image.

Then, as indicated by each dotted arrow 302 in FIG. 3, in order to read the next B-scan image, an irradiation position of the beam of the measurement light 111 is moved by driving the XY-scanner 103 at high speed.

In order to read a 3D-image of the retina, a scanning operation indicated by the arrows 301 and 302 is repeatedly performed.

The center of the beam of the measurement light 111 is adjusted to the center of rotation of the mirror.

When the measurement light 111 is incident upon the eye 105, the measurement light 111 is reflected or scattered by the retina of the eye 105 and turned into the return light 113.

A line camera (referred to also as a two-dimensional image acquisition means or as a fundus image acquisition means) 115 is configured by a lens, a line sensor, an A/D converter, and the like.

Reflection light from the retina irradiated with light rays from an infrared light source (not shown) is reflected by a scanner 118 and guided to the line camera 115. Thus, the reflection light corresponding to each line is read by the line camera 115. The scanner 118 is rotated around an axis parallel to a direction of each line from the line camera 115. Accordingly, an ocular-fundus image (referred to also as a two-dimensional image of the retina or as a retinal image) can be read by the camera 115. The controller 116 joins images respectively corresponding to lines so as to generate a single ocular-fundus image. Every time when an ocular-fundus image is generated, the scanner 118 repeats the action and continues to scan. Consequently, the controller 116 can consecutively acquire ocular-fundus images.

In addition, the controller 116 extracts feature points from the ocular-fundus images according to a known method. Then, the controller 116 detects, from a displacement of each feature point of the consecutively acquired ocular-fundus images, an amount of displacement of an eye due to the involuntary eye movement during visual-fixation. More specifically, a flick motion detection means for detecting a flick motion, among the motions of the involuntary eye movement during visual-fixation, is configured by causing the controller 116 to detect the amount of displacement of an eye due to the involuntary eye movement during visual-fixation.

Figure 4A:
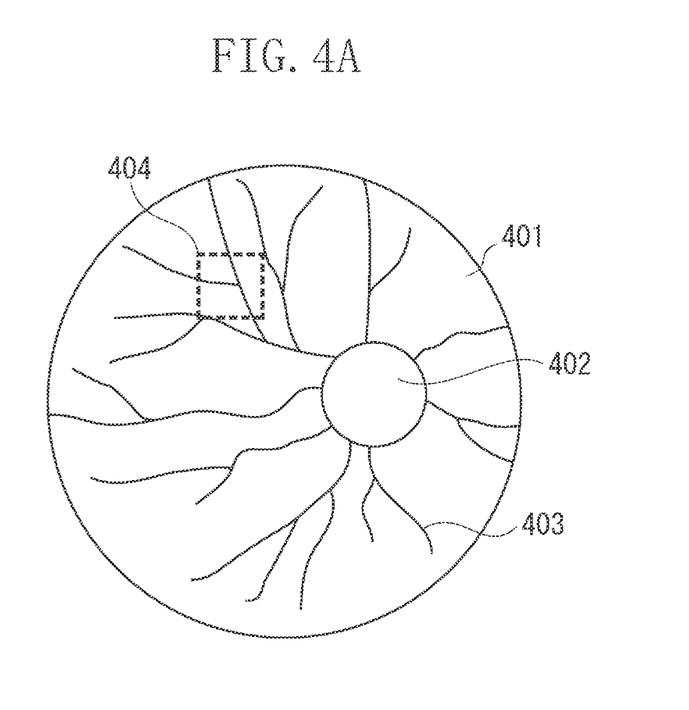
FIGS. 4A, 4B, and 4C illustrate two-dimensional images of an ocular-fundus read with a line camera of the SD-OCT apparatus according to the first exemplary embodiment of the present invention.
Figure 4B:
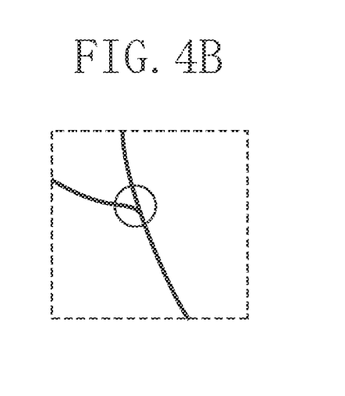
Figure 4C:
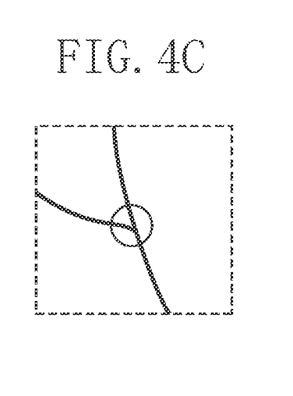

FIGS. 4A, 4B, and 4C illustrate images of an ocular-fundus read by the line camera 115.

FIG. 4A illustrates the entire image of the ocular-fundus. In FIG. 4A, an optic disc 402, retinal blood vessels 403 and a feature region 404 extracted by the controller 116 are shown in a retinal image 401.

Figure 4D:
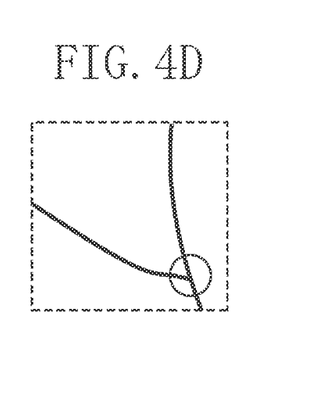

Each of FIGS. 4B, 4C and 4D illustrates the same retinal blood vessels in the retinal feature region 404 shown in an associated one of the consecutively acquired ocular-fundus images.

The controller 116 selects a branch point of the blood vessels encircled in each of FIGS. 4B, 4C, and 4D as a feature point. Then, the controller 116 detects, from a change in coordinates of the branch point, an eye displacement due to the involuntary eye movement during visual-fixation.

As seen from FIGS. 4B, 4C, and 4D, the position of the feature point moves from a leftwardly upper position to a rightwardly lower position.

This means that the eye moves leftwardly and upwardly. The ocular-fundus image is read with a view to detecting a displacement due to the involuntary eye movement during visual-fixation. Accordingly, it is unnecessary to read the entire retina. It is sufficient to determine a reading region in view of an update rate of the ocular-fundus image.

According to the present exemplary embodiment, it is assumed that a region of 1024×1024 pixels is read at a resolution of 10×10 μm every about 10 ms using a line camera having a line rate of 100 kHz. An operation of each of the above units and the like is controlled by a central processing unit (CPU (control means (not shown))) built in the controller 116.

More specifically, the apparatus is configured such that after an end of the flick motion is detected, the controller (flick motion detection means) 116 can start acquiring a tomographic image of an eye under the control of the CPU (control means).

Figure 5:
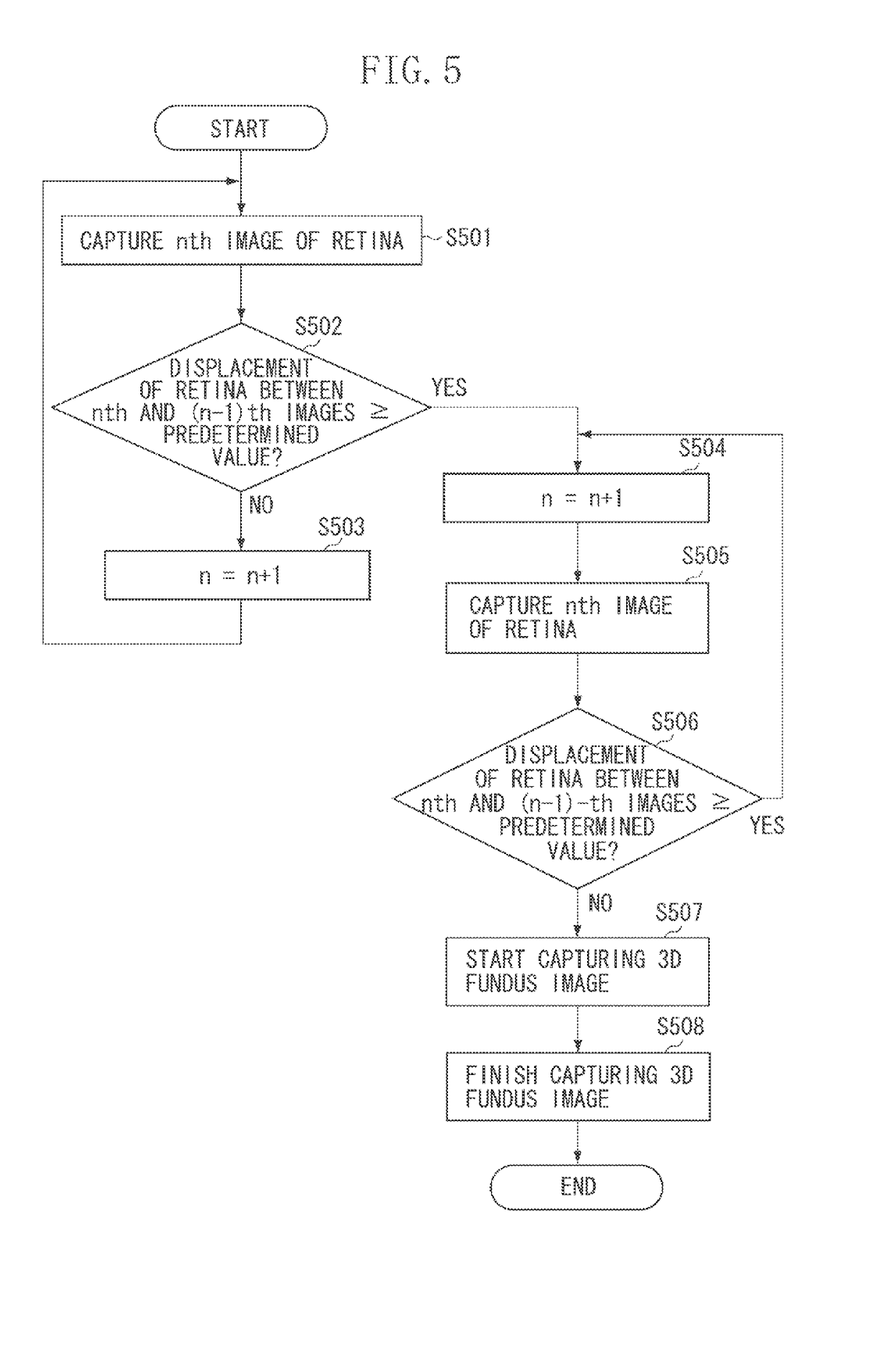
FIG. 5 is a flowchart illustrating a method of imaging an optical coherence tomographic image, which is performed by the SD-OCT apparatus according to the first exemplary embodiment of the present invention.

Next, an imaging method according to the present exemplary embodiment by the SD-OCT apparatus according to the present exemplary embodiment is described with reference to FIG. 5.

First, in step S501, an ocular-fundus image is read using the scanner 118 and the line camera 115 according to an instruction from the controller 116.

Then, in step S502, the feature point of the retina is extracted by the controller 116 in a flick motion detection process. In addition, the controller 116 compares the extracted feature point with that in the immediately preceding ocular-fundus image and determines whether a displacement of the feature point is equal to or more or less than a predetermined value.

The predetermined value is a value to distinguish the flick from the other motions of the involuntary eye movement, i.e., from the drift and the tremor.

According to the present exemplary embodiment, the predetermined value is assumed to be 5 μm, based on the update rate of the ocular-fundus image, which is 10 ms, and the features of the involuntary eye movement during visual-fixation, which are described in FIG. 2C.

If a control-variable n=0, i.e., if the reading of a retinal image is started, there is no image of the immediately preceding frame. Thus, it is determined that the amount of the displacement of the feature point is less than the predetermined value.

Next, if it is determined that the amount of the displacement of the retina is less than the predetermined value, i.e., no flicks occur (NO in step S502), in step S503, the control-variable n is incremented by 1. Then, the process returns to step S501 in which the next ocular-fundus image is captured.

Then, the capturing of the ocular-fundus image is continued in steps S501 through S503 until it is determined that the amount of the displacement of the retina is equal to or more than the predetermined value, i.e., a flick occurs (YES in step S502).

On the other hand, if it is determined that the amount of the displacement of the retina is equal to or more than the predetermined value, i.e., a flick occurs (YES in step S502), in step S504, the control-variable n is incremented by 1. Then, in step S505, the next ocular-fundus image is captured. Next, in step S506, it is determined whether the amount of the displacement of the feature point on the retina is equal to or more than the predetermined value.

Then, if it is determined that the amount of the displacement of the feature point on the retina is equal to or more than the predetermined value, i.e., a flick is being caused (YES in step S506), the process returns to step S504 in which the control-variable n is incremented by 1. Next, in step S505, the next ocular-fundus image is captured. Then, execution of a loop including steps S504 through S506 is continued until it is determined that the amount of the displacement of the retina is less than the predetermined value, i.e., the flick is terminated (NO in step S506).

Next, in the process of imaging a tomographic image, if it is determined that the amount of the displacement of the retina is less than the predetermined value, i.e., 5 μm based on the features of the involuntary eye movement during visual-fixation, in other words, the flick is terminated (NO in step S506), a start-up signal 117 is output from the controller 116 to the XY-scanner 103.

Then, in step S507, imaging of a 3D-image of the ocular-fundus is started. Next, in step S508, an operation of the apparatus is terminated when the imaging of a 3D-image of the ocular-fundus is finished.

In the above exemplary embodiment, thresholds for determining whether a flick motion is started or ended are set in steps S502 and S506 at the same value. However, the thresholds are not necessarily set at the same value.

In the above exemplary embodiment, the line camera 115 and the scanner 118 are used as means for detecting the displacement of an eye. However, if the scanner 118 is set to two-dimensionally scan, a photoelectric conversion element can be used instead of the line camera 115, i.e., the line sensor. In addition, an area sensor configured to directly read an image of an oracular-fundus can be used.

An example of an apparatus configured to continue to measure an involuntary eye movement during visual-fixation even when a 3D-image of an oracular-fundus is being acquired differently from the first exemplary embodiment, is described as a second exemplary embodiment of the present invention.

In the foregoing description of the first exemplary embodiment, it has been described a method for imaging, when the imaging of a 3-D image of an oracular-fundus is started after a flick is finished, the entire predetermined region of an image of an oracular-fundus as it is, without measuring an involuntary eye movement during visual-fixation. However, the 3D-imaging of an oracular-fundus, and the measurement of an involuntary eye movement during visual-fixation, can be performed independent of each other. Thus, a method for continuing, even while the 3D-imaging of an oracular-fundus is performed, the measurement of an involuntary eye movement during visual-fixation, is effective.

More specifically, even in a time-period since the start of the 3D-imaging of an oracular-fundus in step S507 until the end of the 3D-imaging in step S508, the controller 116 continues to cause the line camera 115 and the scanner 118 to operate, and also continues to detect whether a flick occurs.

In this case, it is enough to determine whether an eye movement extremely affecting an image of an oracular-fundus is caused. Accordingly, it is sufficient to repeatedly perform, during an operation in steps S507 and S508 illustrated in FIG. 5, an operation in steps S501 through S503.

If an eye movement extremely affecting an image of an oracular-fundus is caused during the 3D-imaging, it is advisable to issue a measurer a warning indicating that the 3D-imaging is stopped, and to, e.g., start the 3D-imaging over again.

A value differing from 5 μm employed as a pre-imaging threshold can be used as a threshold for detecting a displacement of a retina during 3D-imaging.

While the present invention has been described with reference to exemplary embodiments, it is to be understood that the invention is not limited to the disclosed exemplary embodiments. The scope of the following claims is to be accorded the broadest interpretation so as to encompass all modifications, equivalent structures, and functions.

This application claims priority from Japanese Patent Application No. 2009-262394 filed Nov. 17, 2009, which is hereby incorporated by reference herein in its entirety.

What is claimed is:

1. An ophthalmic imaging method for acquiring a tomographic image of a subject's eye based on interference light generated by interference between return light from the subject's eye irradiated with measurement light and reference light corresponding to the measurement light, the imaging method comprising:

detecting a flick motion among motions of a subject's involuntary eye movement during visual-fixation, wherein the flick motion indicates an amount of displacement of the subject's eye per unit time equal to or more than a predetermined value;

acquiring a three-dimensional tomographic image of the subject's eye in a case where an end of the flick motion is detected in the detecting the flick motion; and stopping acquiring the three-dimensional tomographic image in a case where a start of the flick motion is detected during acquisition of the three-dimensional tomographic image, and starting acquiring a three-dimensional tomographic image of the subject's eye over again when an end of the flick motion is detected again.

2. The ophthalmic imaging method according to claim 1, further comprising acquiring consecutive images of a fundus of the subject's eye, and using the acquired images of the fundus; and wherein in a case where an amount of displacement of the acquires consecutive images is equal to or more than the predetermined value, detecting the flick motion in the detecting the flick motion.

3. The ophthalmic imaging method according to claim 1, wherein, in a case where the end of the flick motion is detected, acquisition of the three-dimensional tomographic image is started in the acquiring the three-dimensional tomographic image by outputting a signal to a scanning unit configured to scan with the measurement light, wherein the detecting of the flick motion is continued even during acquisition of the three-dimensional tomographic image.

4. A program stored in a non-transitory tangible computer-readable storage medium for causing a computer to execute an ophthalmic imaging method according to claim 1.

5. The ophthalmic imaging apparatus according to claim 1, wherein the predetermined value is used to distinguish the flick motion from a drift motion and a tremor motion among motions of the subject's involuntary eye movement during visual-fixation.

6. The ophthalmic imaging method according to claim 1, further comprising:
   extracting a feature regions from each of the images of the ocular-fundus; and
   determining whether an amount of displacement between the images of the ocular-fundus is equal to or more than the predetermined value based on the feature region,
   wherein a start and an end of the flick motion is detected based on a result of determination in the determining.

7. The ophthalmic imaging method according to claim 6, wherein a part of an image corresponding to a branch of a blood vessel of an ocular-fundus of the subject's eye from each of the images of the ocular-fundus, as the feature region.

8. The ophthalmic imaging method according to claim 1, further comprising: issuing a warning about a start of the flick motion in a case where a start of the motion is detected during acquisition of the three-dimensional tomographic image.

9. The ophthalmic imaging method according to claim 1, wherein starting acquiring a three-dimensional tomographic image of the subject's eye over again from beginning when an end of the flick motion is detected again.

10. An ophthalmic imaging apparatus for acquiring a tomographic image of a subject's eye based on interference light generated by interference between return light from the subject's eye irradiated with measurement light, and reference light corresponding to the measurement light, comprising:
   a detection unit configured to detect a flick motion among motions of subject's eye movement during visual fixation, wherein the flick motion indicates an amount of displacement of the subject's eye per unit time is equal to or more than a predetermined value; and
   a control unit configured to acquire a three-dimensional tomographic image of the subject's eye in a case where an end of the flick motion is detected, to stop acquiring the three-dimensional tomographic image in a case where a start of the flick motion is detected during acquisition of the three-dimensional tomographic image, and start acquiring a three-dimensional tomographic image of the subject's eye over again when an end of the flick motion is detected again.

11. The ophthalmic imaging apparatus according to claim 10, wherein the predetermined value used to distinguish the flick motion from a drift motion and a tremor motion among motions of the subject's involuntary eye movement during visual-fixation.

12. The ophthalmic imaging apparatus according to claim 10, further comprising:
   an ocular-fundus image acquisition unit configured to acquire temporally-consecutive images of an ocular-fundus of the subject's eye,
   wherein the detection unit detects an end of the flick motion using the images of the ocular-fundus acquired by the ocular-fundus image acquisition unit in a case where the amount of displacement of the flick motion is less than the predetermined value.

13. The ophthalmic imaging apparatus according to claim 10, further comprising:
   an imaging termination unit configured to finish imaging of the subject's eye according to a result of the detection by the detection unit when the mount of movement, which is equal to or more than the predetermined value, is detected by the detection unit while consecutively acquiring a plurality of tomographic images of the subject's eye.

14. The ophthalmic imaging apparatus according to claim 12, further comprising:
   an extraction unit configured to extract a feature regions from each of the images of the ocular-fundus; and
   a determination unit configured to determine whether an amount of displacement between the images of the ocular-fundus is equal to or more than the predetermined value based on the feature region,
   wherein the detection unit detects a start and an end of the flick motion based on a result of determination by the determination unit.

15. The ophthalmic imaging apparatus according to claim 14, wherein the extraction unit extracts, as the feature region, a part of an image corresponding to a branch of a blood vessel of an ocular-fundus of the subject's eye from each of the images of the ocular-fundus.

16. The ophthalmic imaging apparatus according to claim 10, wherein the control unit outputs a signal to a scanning unit configured to scan with the measurement light and starts acquiring a three-dimensional tomographic image of the subject's eye in a case where an end of the flick motion is detected.

17. The ophthalmic imaging apparatus according to claim 10, wherein the control unit starts acquiring a three-dimensional tomographic image of the subject's eye over again from beginning when an end of the flick motion is detected again.

18. The ophthalmic imaging apparatus according to claim 10, wherein the control unit issues a warning about a start of the flick motion in a case where a start of the flick motion is detected during acquisition of the three-dimensional tomographic image.

19. An optical coherence tomographic image imaging method for acquiring a tomographic image of a subject's eye based on combined light of return light from the subject's eye irradiated with measurement light and reference light corresponding to the measurement light, the method comprising:
   acquiring temporally-consecutive images of an ocular-fundus of the subject's eye;
   detecting an end of a flick motion based on the images of the ocular fundus, in a case where a value of the flick motion becomes less than a predetermined value during the flick motion having an amount of displacement per unit time among motions of the subject's involuntary eye movement during visual-fixation equal to or more than the predetermined value;
   outputting a signal to a scanning unit configured to scan with the measurement light and starting acquiring a three-dimensional tomographic image of the subject's eye, in a case where an end of the flick motion is detected;
   continuing to detect the flick motion during acquisition of the three-dimensional tomographic image and detecting a start of the flick motion based on the images of the ocular-fundus; and
   stopping acquiring the three-dimensional tomographic image in a case where a start of the flick motion is detected during acquisition of the three-dimensional tomographic image, and starting acquiring a three-dimensional tomographic image of the subject's eye over again when an end of the flick motion is detected again.

20. A non-transitory computer-readable storage medium having a program stored thereon for causing a computer to execute an optical coherence tomographic image imaging method according to claim 19.

21. The optical coherence tomographic image imaging method according to claim 19, wherein starting acquiring a three-dimensional tomographic image of the subject's eye over again from beginning.

22. An ophthalmic imaging method for acquiring a tomographic image of a subject's eye based on interference light generated by interference between return light from the subject's eye irradiated with measurement light and reference light corresponding to the measurement light, the imaging method comprising:
  acquiring a three-dimensional tomographic image of the subject's eye;
  detecting an eye motion during acquisition of the three-dimensional tomographic image, wherein the eye motion indicates an amount of displacement of the subject's eye equal to or more than a threshold value; and
  stopping acquiring the three-dimensional tomographic image in a case where the eye motion is detected, and starting acquiring a three-dimensional tomographic image of the subject's eye over again from beginning.

23. A non-transitory computer-readable storage medium having a program stored thereon for causing a computer to execute an ophthalmic imaging method according to claim 22.

24. An ophthalmic imaging apparatus for acquiring a tomographic image of a subject's eye based on interference light generated by interference between return light from the subject's eye irradiated with measurement light and reference light corresponding to the measurement light, comprising:
  an acquiring unit configured to acquire a three-dimensional tomographic image of the subject's eye;
  a detection unit configured to detect an eye motion during acquisition of the three-dimensional tomographic image, wherein the eye motion indicates an amount of displacement of the subject's eye equal to or more than a threshold value; and
  a control unit configured to stop acquiring the three-dimensional tomographic image in a case where the eye motion is detected, and start acquiring a three-dimensional tomographic image of the subject's eye over again from beginning.

25. An optical coherence tomographic image imaging apparatus for acquiring a tomographic image of a subject's eye based on combined light of return light from the subject's eye irradiated with measurement light and reference light corresponding to the measurement light, the apparatus comprising:
  an acquiring unit configured to acquire temporally-consecutive images of an ocular-fundus of the subject's eye;
  a detecting unit configured to detect an end of a flick motion based on the images of the ocular fundus, in a case where a value of the flick motion becomes less than a predetermined value during the flick motion having an amount of displacement per unit time among motions of the subject's involuntary eye movement during visual-fixation equal to or more than the predetermined value;
  an outputting unit configured to output a signal to a scanning unit configured to scan with the measurement light and starting acquiring a three-dimensional tomographic image of the subject's eye, in a case where an end of the flick motion is detected;
  a continuing unit configured to continue to detect the flick motion during acquisition of the three-dimensional tomographic image and detecting a start of the flick motion based on the images of the ocular-fundus;
  a control unit configured to stop acquiring the three-dimensional tomographic image in a case where a start of the flick motion is detected during acquisition of the three-dimensional tomographic image, and to start acquiring a three-dimensional tomographic image of the subject's eye over again when an end of the flick motion is detected again.

26. The optical coherence tomographic image imaging apparatus according to claim 25, wherein the control unit starts acquiring a three-dimensional tomographic image of the subject's eye over again from beginning.

\* \* \* \* \*